(12) United States Patent
Alt et al.

(10) Patent No.: US 6,251,134 B1
(45) Date of Patent: Jun. 26, 2001

(54) STENT WITH HIGH LONGITUDINAL FLEXIBILITY

(75) Inventors: Eckhard Alt, Ottobrunn; Andreas Poesel, Munich, both of (DE)

(73) Assignee: Inflow Dynamics Inc., Springfield, VA (US)

( * ) Notice: Subject to any disclaimer, the term of this patent is extended or adjusted under 35 U.S.C. 154(b) by 0 days.

(21) Appl. No.: 09/259,904

(22) Filed: Feb. 28, 1999

(51) Int. Cl.$^7$ ...................................................... A61F 2/06
(52) U.S. Cl. ........................ 623/1.16; 623/1.19; 623/1.2; 606/194; 606/195; 606/198
(58) Field of Search ........................ 606/108, 191–194, 606/198, 195; 623/1

(56) References Cited

U.S. PATENT DOCUMENTS

| | | | |
|---|---|---|---|
| 5,041,126 | * | 8/1991 | Gianturco .............................. 606/195 |
| 5,879,370 | * | 3/1999 | Fischell et al. ....................... 606/198 |
| 5,879,381 | * | 3/1999 | Moriuchi et al. .......................... 623/1 |
| 5,911,754 | * | 6/1999 | Kanesaka et al. .................... 606/198 |
| 6,017,365 | * | 1/2000 | Von Oepen ........................... 606/194 |

FOREIGN PATENT DOCUMENTS

98/20810 * 5/1998 (WO) ................................ A61F/2/06

* cited by examiner

Primary Examiner—Gary Jackson

(57) ABSTRACT

A stent of high longitudinal flexibility includes multiple ring elements coupled together to be articulating without fixed physical attachment therebetween when the stent is in an unexpanded state, and to uncouple automatically while maintaining their positional relationship when the stent is deployed to an expanded state. The stent is fabricated to offer radial strength suitable for supporting a wall of a vessel, duct or tract of a patient in which the stent is to be implanted, against recoil of the wall in response to deployment of the stent. The fabrication process includes forming a plurality of common ring elements aligned along a longitudinal axis; and fashioning coupling elements on each of the ring elements to mate with and pivot longitudinally relative to coupling elements fashioned on neighboring ring elements without fixed physical attachment between the coupling elements. The coupling elements are constructed to allow withdrawal from their mating relationship when the ring elements are substantially uniformly expanded in diameter during deployment of the stent for complete separation of the ring elements from one another when the stent is in an expanded state. The ring elements may be formed collectively from a hollow tube, with the coupling elements fashioned concurrently therewith; or the ring elements may be formed individually with the respective coupling elements thereon, and subsequently snapped together in longitudinal axial alignment.

30 Claims, 2 Drawing Sheets

STENT WITH HIGH LONGITUDINAL FLEXIBILITY

BACKGROUND OF THE INVENTION

The present invention relates generally to stents which are implantable or deployable in a vascular or endoluminal location within the body of a patient to maintain the lumen open at that site, and more particularly to improvements in stent flexibility, particularly longitudinally.

Stents are expandable prostheses employed to maintain narrow vascular and endoluminal ducts or tracts of the human body open and unoccluded, such as a portion of the lumen of a coronary artery after dilatation of the artery by balloon angioplasty. While vascular usage is frequently discussed in this application, it will be understood by those skilled in the art that stents having the characteristics and features of the present invention may be implanted in other ducts or tracts of the human body to keep the lumen open, such as in the tracheobronchial system, the billiary hepatic system, the esophageal bowel system, and the urinary tract system.

In the case of an occluded coronary artery, for example, the original blockage is typically attributable to fat deposits or plaque on the inner lining of the vessel. A new blockage often occurs after an angioplasty procedure is performed to compress the deposits against the inner lining of the vessel, as by use of balloon angioplasty, or to virtually entirely remove the deposits, as by use of laser angioplasty or rotational cutting. The blood vessel wall is subjected to trauma by such procedures, leading to neointimal hyperplasia, i.e., rapid cellular proliferation in the affected region of the wall, and thereby causing restenosis and re-occlusion of the vessel lumen in a significant percentage of angioplasty patients within a period of from three to six month s following the initial procedure.

To avoid this re-occlusion and to maintain the lumen of the vessel open, it is customary procedure to install a stent at the angioplasty site in the vessel. The stent is deployed by radial expansion of its wall as pressure is exerted by controlled inflation of the balloon of a balloon catheter on which the stent is mounted. In this way, the stent wall is caused to engage the inner lining or surface of the vessel wall with sufficient resilience to allow some contraction and, desirably, with sufficient stiffness to resist or minimize the natural recoil of the vessel wall. Recoil is the reaction of the vessel wall to an even slight expansion of its diameter when the stent is deployed, owing to the elastic retraction force of the vessel wall. Recoil produces a re-narrowing of the vessel after the stent is implanted compared to the vessel diameter when the balloon is inflated.

The stent provides not only the benefits of reducing restenosis following vascular intervention such as a coronary angioplasty, but also reduces acute complications such as acute vessel closure. Widespread use of stents has demonstrated their benefit in applications beyond merely coronary implantations, such as in iliac, femoral, infragenouidal, carotid and other vascular applications. Additionally, stents have been found to be important in treating other vessels and ducts, such as biliary, esophageal and tracheal applications, to mention a few. In these applications also, the primary purpose of the stent is to keep open a lumen that might otherwise become occluded by a neoplasia.

Nevertheless, some limitations remain in current methods of use of stents. Although the extent of restenosis of the vessel is reduced, its remaining impact is of sufficient magnitude to represent a serious medical and economic problem. A principal part of the problem is attributable to individual patient-related factors, such as vessel size, diabetes, degree of stenosis prior to the intervention, and the type, length and morphology of the lesion (i.e., the region of narrowing that prompted the intervention). The problem is also attributable in significant part to stent-related factors of a mechanical nature. These include force distribution of the implanted stent on the vessel wall, symmetry of opening of the stent, metal surface and geometric design creating sharp edges and corners.

Some current stent designs have sought to provide high mechanical stability for resisting recoil after stent implantation. The two counter-acting forces, one being the elastic recoil exhibited by the highly overexpanded vessel wall and the other being the radial strength of the expanded stent, are being brought to a state of balance. Stent designs of the slotted tube and multicellular types have provided suitable mechanical stability. Slotted tube stent designs utilize a plurality of slots which are disposed substantially parallel to the longitudinal axis of the tubular member. Depending on the length of the lesion at the site to be treated, it may be necessary to implant more than one stent in longitudinal alignment. To achieve greater longitudinal flexibility, adjacent stents may be connected by connecting members of the type described in European Patent Application No. 89118069.7 of R. Schatz for Expandable Intraluminal Graft.

U.S. Pat. No. 5,304,200 to R. Spaulding describes a stent with a plurality of adjacent generally circumferential sections that are substantially axially positioned with respect to each other. The terminal portions of the end circumferential sections are welded directly to a portion of a generally adjacent circumferential following section.

European Patent Application No. 92309822.2 to L. Lau et al describes an expandable stent with circumferential bending rings interconnected to each other by connecting members, which are offset from face to face.

U.S. Pat. No. 5,824,045 to E. Alt describes a slotted tube stent in which circumferential sinusoidal rings are interconnected to each other, and a gold coating is applied to enhance visibility and reduce thrombogenicity.

U.S. Pat. No. 5,827,321 to G. Roubin et al describes an intraluminal prosthesis in which a plurality of connecting members connect the a pieces of adjacent annular members, the connecting members having a plurality of alternating segments that function to compensate for the smaller longitudinal dimension of each annular member in the expanded state.

U.S. Pat. No. 5,843,117 to E. Alt describes a stent with serpentines that are substantially devoid of sharp corners and edges, where each serpentine has an oval cross-section, and adjacent serpentines are joined together at crest and trough respectively so that their interconnections are 180° out of phase relative to their wavelength.

In addition to the type of multicellular or tubular stent that provides high mechanical strength and low recoil, a second type of stent known as a coil stent has been described in the prior art.

U.S. Pat. No. 4,886,062 to D. Wiktor describes a vascular stent comprising a cylindrical open-ended wire component in a zig-zag pattern to allow for radial expansion without significantly shortening its length, and in which a single filament continuous from one end to the other forms the support structure. Such a stent has an advantage of increased longitudinal flexibility, but at a sacrifice of radial support owing to absence of an annular structure.

A similar type of stent is described in U.S. Pat. No. 5,370,683 to A. Fontaine, in which the stent is formed from a single filament of low memory biocompatible material having a series of U-shaped bends, the filament being wrapped around the mandril in circumferential fashion so that the curved portions of each bend are aligned. This stent similarly retains high flexibility but suffers from lack of a ring structure to increase support and reduce recoil.

U.S. Pat. No. 5,591,230 to J. Horn also describes a stent fabricated from a single filament wire, where the wire forms an original multi-loop design including a plurality of concentric bended loops in a continuous wire folded along a length thereof Like the two immediately preceding patented designs, this stent design provides longitudinal flexibility but less radial support.

Although the best clinical results appear thus far to have been achieved with the multicellular designs, and coil stents have been found to achieve less favorable long-term outcome after implantation in the patient's coronary system from the standpoints of restenosis and complication rate, none of the current stent designs seem to pay sufficient attention to the biomechanics of the native human coronary vessel. A rigid tubular stent undergoes little mechanical bending longitudinally when implanted in the coronary ostium, but encounters a problem when implanted for treatment of a more distal coronary lesion because of increased longitudinal bending of the vessel. The native coronary vessels in patients with hypertension, in particular, exhibit increased bending with considerable changes in the radius of the bend following systole and diastole. The coronary vessel flexes more than 100,000 times a day following myocardial contraction—more than 400 million in ten years. Implantation of a relatively rigid stent, or any stent with severely limited longitudinal flexibility, in this region of increased mechanical stress creates a substantial problem because the bending is not equally distributed over the entire length of the stent. Rather, bending is primarily limited to two major points at the proximal and distal ends of the stent, in the transition between the edges of the stent and the vessel. The increased mechanical stress in this region represents an increased risk for restenosis, especially when bifurcations are also involved.

A representative example of a prior art stent is illustrated in FIG. 1. Spaced-apart, circumferentially disposed, identical sinusoidal ring structures 10 are stacked longitudinally and have their respective crests 12 and troughs 13 aligned longitudinally. Adjacent pairs of individual rings such as 11, 14 and 17 are interconnected crest-to-crest or trough-to-trough by straight longitudinal elements such as 15, 16 and 18, 19, in which the interconnecting elements 15, 16 are offset from interconnecting elements 18, 19 to allow more longitudinal flexibility of the overall structure. Some of the interconnecting elements may be bent, rather than straight, such as the elements 21, 22 connecting rings 17 and 20. Although this prior art design allows some flexibility when implanted, the compliance of the expanded stent is considerably less than the compliance of the natural vessel in which it is implanted, particularly in the aforementioned regions of increased mechanical stress.

A significant problem with stent designs exemplified by that of FIG. 1 is that improvement in longitudinal flexibility requires that the interconnecting elements 15, 16, 18, 19, 21, 22 be made very thin. Since the coronary vessels as well as other vessels in the cardiovascular system undergo longitudinal bending at the rates mentioned above, it is clear that mechanical limitations impose significant barriers to making the interconnecting elements very thin and flexible.

Therefore, the principal aim of the present invention is to provide a stent design that offers considerable mechanical support against inwardly directed radial forces as occur with vessel recoil, and gives excellent coverage of the narrowed vessel region to diminish local wall stress, but which also allows optimum longitudinal flexibility of the vessel to avoid compromising the natural bending of the vessel and the implanted stent that occurs with systolic and diastolic contractions and relaxations of the heart.

A further aim of the invention is to maintain the mechanical integrity and stability of such a stent in the process of fabricating the stent and mounting it on a balloon or other means by which the stent is to be implanted in the patient's body, but to release or surrender this mechanical stability when the stent is implanted and deployed at the preselected site in the vessel, duct, tract or orifice of the body at which the stent is designed to perform its primary function (i.e., the target site).

SUMMARY OF THE INVENTION

According to the invention, a stent of high longitudinal flexibility adapted to be implanted in a vessel, duct, tract or orifice of a human body to maintain an open lumen therein at a target site of final deployment, with a first small diameter unexpanded state for advancement to the target site and a second relatively larger diameter expanded state of deployment at the target site, has a highly articulated configuration of multiple ring elements coupled together in longitudinal pivotal relation without fixed physical attachment therebetween while the stent is in its unexpanded state. In a preferred embodiment, the ring elements are substantially identical and commonly aligned along a longitudinal axis of the stent. Each of the couplings releases or separates when the stent is in its expanded state, to cause the ring elements to completely separate from one another for final deployment of the stent while maintaining their positional relation for supporting the lumen wall along the target site.

Each of the ring elements includes a plurality of the couplings circumferentially positioned for mating in longitudinal pivotal relationship with corresponding couplings of at least one adjacent ring. The plurality of couplings on each ring element reside on a plurality of longitudinal projections equally spaced-apart along and connected to a circular lateral portion of the respective ring element. The lateral portion is perpendicular to the longitudinal axis of the stent, and the longitudinal projections each reside parallel to the longitudinal axis of the stent and include a pair of the couplings for mating with corresponding couplings of adjacent rings at opposite sides thereof. The couplings are configured to interlock with the mating couplings of adjacent rings so as to maintain their longitudinal pivotal relationship.

BRIEF DESCRIPTION OF THE DRAWINGS

The above and still further aims, objectives, features, aspects and attendant advantages of the present invention will become apparent from the following detailed description of a preferred embodiment and method of fabrication of a stent in accordance with the invention, constituting the best mode presently contemplated of practicing the invention, when taken in conjunction with the accompanying drawings, in which.

DETAILED DESCRIPTION OF PREFERRED EMBODIMENT AND METHOD

Figure 1:
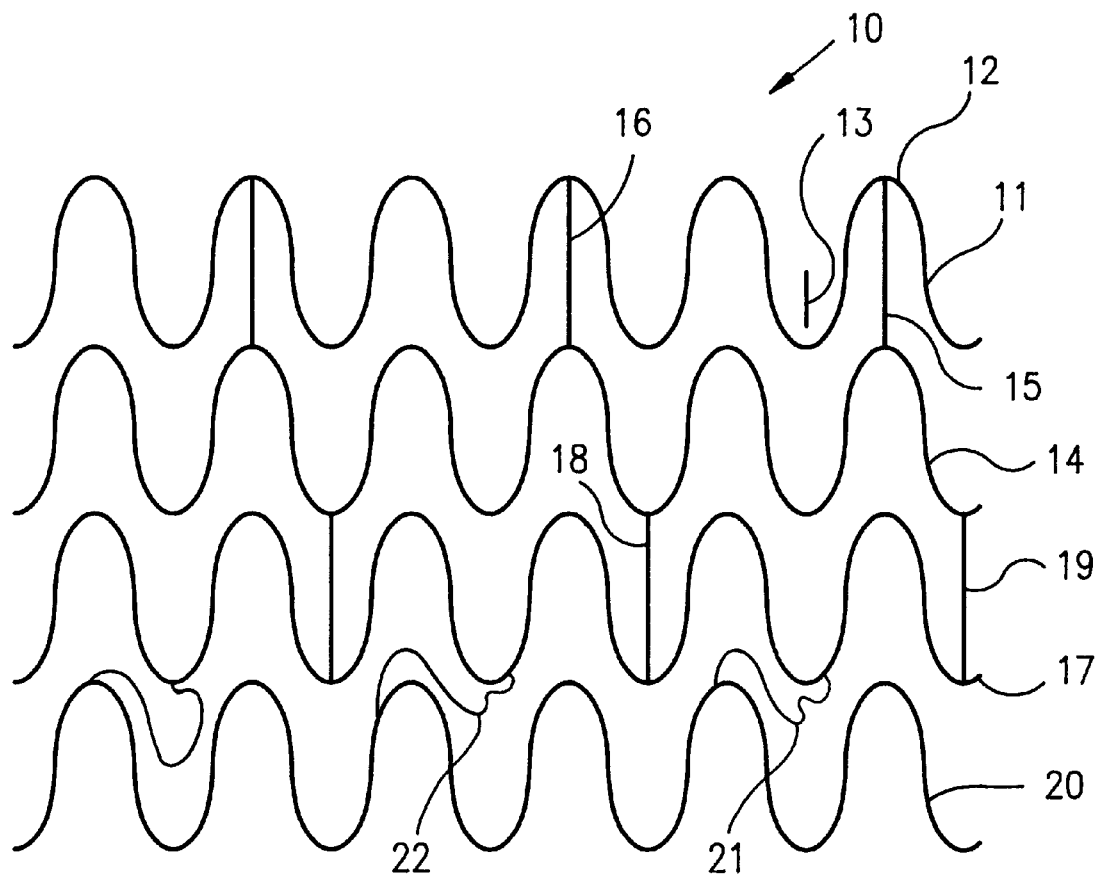
FIG. 1 is an open partial view of the side of an exemplary prior art stent design, described above.
Figure 2:
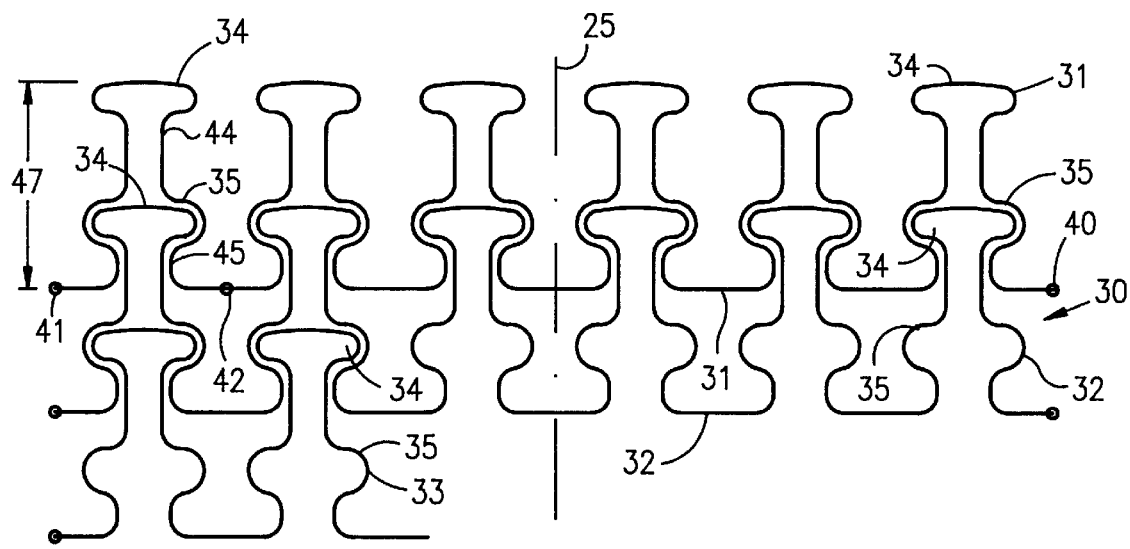
FIGS. 2 and 3 are open flat development views of a portion of the side of a preferred embodiment of a stent according to the present invention, FIG. 2 illustrating the stent in its unexpanded state, and FIG. 3 illustrating the stent in its expanded state.

In FIG. 2, which illustrates an open, flat development view of the side of a stent 30 in a state of fabrication or assembly (and also a state of being crimped, but in any event not in its expanded state by which is meant a state of substantially full deployment), the desired length of stent 30 (according to the region of the target site which it is to occupy) will determine the total number of individual circumferential elements or rings such as 31, 32, 33 which are stacked longitudinally (i.e., along the longitudinal axis) in the overall configuration. A very significant feature of the invention is that the stent is composed of a multiplicity of such circumferential elements, no two or more of which are interconnected by fixed members, i.e., interconnecting members which are fixedly physically attached to one or more of the circumferential elements. Rather, to maintain the geometrical configuration necessary to allow crimping the stent on a balloon and advancing the balloon-mounted stent into a vessel to a target site for deployment, the mechanical contact between adjacent circumferential elements is determined by the special shape of those elements or portions thereof.

In particular, each circumferential element 31, 32, 33 (and so forth, only those three being depicted in the Figure, but it will be understood that many others corresponding to each of those three are included in the longitudinal stacking of the overall stent) is formed in a pattern or shape that enables an interlocking of adjacent elements much like the interlocking pieces of a board puzzle. Circumferential element 32, for example, is defined by a wire or strip which generally extends laterally (i.e., perpendicularly) to the longitudinal axis 25 of the overall stent 30 but which makes periodic identical excursions in a direction parallel to that axis (i.e., longitudinally). These periodic longitudinal excursions or projections have at least a pair of spaced-apart wider (i.e., laterally extending) openings or bows such as 34, 35, one of which may be regarded as a male coupling (in this case, 34) and the other as a female coupling (in this case, 35). It is important to observe that each male coupling 34 is slightly smaller than each female coupling 35 to allow a respective one of the former on one ring to fit within a respective one of the latter on an immediately adjacent ring with some slight tolerance or play (unlike the above analogy to a board puzzle), so that the mated couplings are somewhat loosely but reliably interlocked.

Simply stated, coupling 34 of ring 32 is configured to mate with (i.e., to enter) coupling 35 of adjacent ring 31, and coupling 35 of ring 32 is adapted to mate with (i.e., to receive) coupling 34 of oppositely adjacent ring 33. These couplings thus interlock but have a certain freedom to move by pivoting longitudinally relative to their respective mates, and no coupling or the ring of which it is a part is fixedly attached to a coupling of any other ring.

As viewed in the embodiment of FIG. 2, the illustration is a development Figure and it will be understood that the manufacturing process results in a stent in which the actual elements are circular, one end of the flat configuration in the Figure being connected to the other end, as at points 40 and 41 for circumferential element 31. In practice, individual circumferential elements may be strips of material fabricated from a hollow tube composed of medical grade stainless steel, titanium, iridium, nickel-titanium alloy (Nitinol) or derivatives thereof or other conventional stent material, by laser cutting, mechanical stanzen or chemical etching utilizing known process technology. If the rings are collectively fabricated in such manner, they will be interlocked by their respective mating couplings at the outset. If the rings are individually fabricated, however, it will be necessary to perform an assembly in which they are snapped together to form the overall longitudinally-oriented stent. This may be done by depressing a point on the side of the ring sufficiently to bend it inwardly and thereby reduce its diameter to slightly less than that of the ring with which it is to be coupled, and then snapping the coupling elements in place to return the ring to its original diameter. In either event, the individual circumferential elements are readily provided with rounded corners and edges by a conventional process of electropolishing.

Alternately, each of the individual rings may be formed in an initially flat development from a single wire, and the ends thereof then laser welded together to form the circular configuration for the respective ring. The butt weld, whether of a wire embodiment or a strip embodiment, may then be polished to give that region the same general dimension(s) as the remainder of the element. Assembly of the individual wire rings into a multi-ring stent would then be performed in a manner identical to that described above for the individually fabricated strip rings.

In the embodiment illustrated in FIG. 2, each ring of the stent has six longitudinal projections, each of which is aligned with corresponding identical projections on each of the other rings. If such a stent is to be crimped on a balloon of 1 mm diameter, the total circumference of the stent and each ring thereof is about 3.14 mm ($2\pi r$). In that case, the distance between the center lines of adjacent coupling elements on the same ring would be 3.14 mm/6=0.5 mm (approx)=500 microns. The thickness of the individual strip or strut in each ring or coupling element thereof is preferably in a range from 80 to 120 microns.

The invention is not limited to the exact configuration of the embodiment shown in FIG. 2. For example, although it is more convenient for the sake of fabrication, assembly (which would be required if individual rings are fabricated separately) and ultimate deployment, the longitudinal projections on each circumferential element need not extend in the same direction but may, instead, be alternated in one direction and the opposite direction. In that circumstance, the end rings of the stent could be fabricated with a continuous band in place of the last set of coupling elements.

The configuration of the stent illustrated in FIG. 2 represents the stent in its unexpanded state, e.g., states of fabrication and assembly, and also in a crimped state as it would be when mounted on a balloon of an implant catheter, albeit the elements might be slightly more compressed without interfering with the capability of the coupling elements to pivot longitudinally in their mating relationship. While in an unexpanded state, the individual rings such as 31, 32, 33 cannot slide along the longitudinal axis of the stent, except together with the entire stent, since the couplings or coupling elements 34, 35 of adjacent rings are mated in interlocking relationship. However, the capability of these mated couplings to pivot longitudinally relative to one another, without being impeded by any fixed physical attachment, provides the stent with a property of articulation and optimum flexibility to be advanced through the tortuous paths often encountered during implantation, particularly in the vascular system of the body.

It is another significant feature of the invention that this optimum flexibility of the stent in the crimped state is matched by an optimum flexibility of the stent when in its expanded state, i.e., when the stent is deployed (fully or substantially so) at a target site in the vessel by inflating the balloon on which it is mounted or otherwise exerting symmetrical radial forces from within the lumen of the stent to expand its diameter (including through a technique such as self-expansion) until it is positioned firmly against the interior surface of the wall of the vessel.

Figure 3:
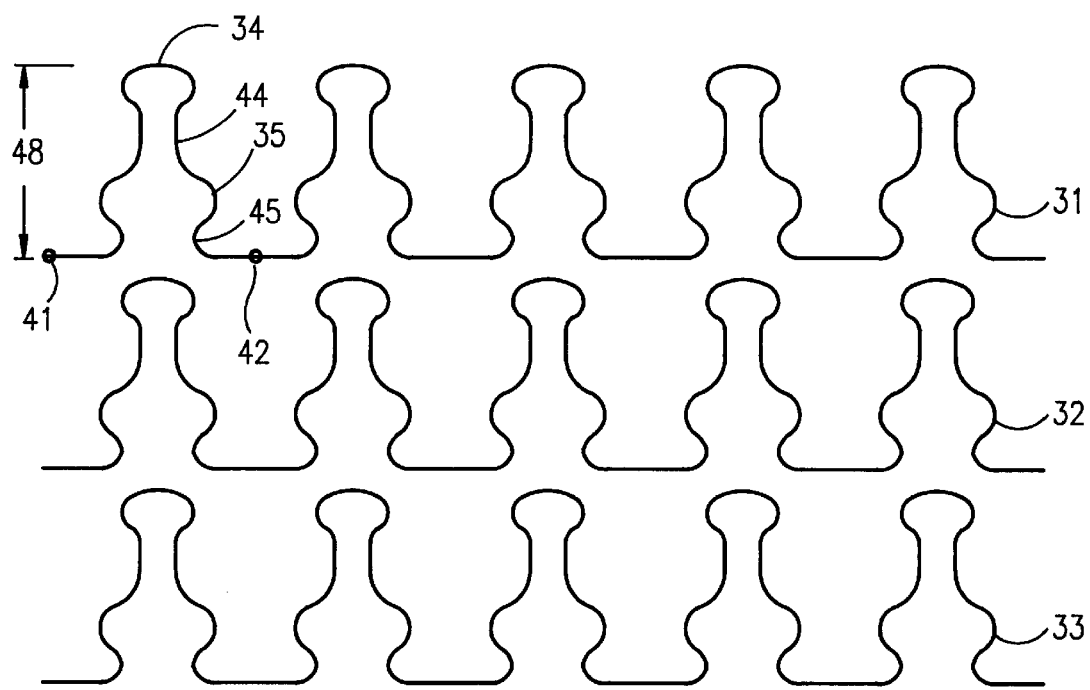

Referring now to FIG. 3, as the stent is expanded for deployment the coupling elements undergo a change in shape dictated by the increase in stent diameter and interrelated increase in stent (and each ring's) circumference. The coupling elements 34 go from a bow-like or cap-like shape shown in FIG. 2 to the laterally narrower (longitudinally elongated) loop shape shown in FIG. 3. The coupling elements 35 also undergo a change in shape from the bow-like appearance of (albeit slightly larger than) element 34, but to a less well-defined rounded shoulder shape. The difference in shape assumed by these two coupling elements on each longitudinal projection during stent expansion is primarily a function of their respective locations on the projection and the closer position of coupling element 35 to the main, generally lateral portion of the strip or wire that forms the respective ring. In any event, these changes in shape occur in a relatively symmetrical fashion, so that the rings retain their positions relative to one another (i.e., their positional relationships) without skewing or twisting. This is assured by virtue of the stent's captive position between the balloon on which it is mounted (i.e., extending through the lumen of the stent) and the interior surface of the vessel wall with which it is coming into engagement.

The total length laterally from center to center between adjacent longitudinal projections of a ring such as 31, in going from a crimped (unexpanded) state to a fully deployed (expanded) state, is represented by the distance between points 41 and 42 in FIGS. 2 and 3, respectively. It will be observed from these Figures that this lateral length, which is a portion of the circumference of the ring, increases with the uniform expansion of the stent (and ring) diameter during deployment, as is to be expected. This is a result of the opening of the bow-like coupling elements 34 and 35 longitudinally and the concomitant lateral widening of the neck portion 44, 45, respectively, immediately below each coupling element as the radially outwardly directed forces of expansion are taking place.

It is also to be expected that as the diameter of a stent is expanded in deployment, its length will decrease from that in which the stent was in the crimped or manufactured state unless special techniques of stent design are undertaken in an effort to maintain a near constant length or at least to compensate elsewhere to avoid a significant reduction in stent length. For the stent design of the present invention, the compensation in length for the increased diameter is provided by a withdrawal of the male coupling elements 34 of each ring from the female coupling elements 35 of the adjacent ring as the shapes of the coupling elements change in the aforementioned manner during stent expansion. This is shown quite clearly in FIG. 3. In fact, the length of the longitudinal projections in the crimped state and the expanded state, as represented by lengths 47 and 48 in FIGS. 2 and 3, respectively, changes very little, with the latter being slightly less than the former. As coupling elements 34 and 35 undergo some lateral narrowing and longitudinal lengthening, neck portions 44 and 45 undergo some lateral widening and longitudinal shortening, which tends to maintain the status quo on length. What does change, however, is that the adjacent rings such as 31, 32 and 32, 33 are now separated from one another, albeit remaining in very close proximity longitudinally. This complete separation of the rings resulting from release of the couplings can be arranged by appropriate dimensioning to occur at a time just before complete deployment, so that the rings are allowed to separate and still retain their positional relation as they engage tissue at the interior surface of the vessel wall, so as to provide homogeneous support to the wall without physically contacting their neighboring rings.

It will be recognized, then, that the stent design of the present invention results in a device of high longitudinal flexibility in the crimped state—even though the stent is mechanically one integral unit in that state by virtue of the puzzle-like interlocking of its pieces—as a consequence of the articulated rings and their capability to pivot longitudinally at their respective coupling elements without the restrictions on movement or bending otherwise imposed by fixed attachments as are generally found in the prior art. This means that the crimped, balloon-mounted stent is readily navigated through even very tortuous vessels, ducts or tracts of the body with considerably less likelihood of injury to the walls thereof or of becoming stuck in a relatively tight turn. And yet that same stent design allows the individual rings to separate completely as the stent is converted to its expanded state during deployment at the preselected target site—which constitutes optimum longitudinal flexibility of the stent—while still providing homogeneous support to the vessel wall in which it is implanted, without physical contact between the rings.

In the expanded, deployed state of the stent of the present invention, then, the distribution of biomechanical stress is not concentrated at the ends of the stent, but rather is equally distributed over the entire length of the stent. And this is true even in those regions of a vessel such as the distal portions of the coronary arteries where the aforementioned high mechanical stress is present.

Although certain preferred embodiments and methods have been disclosed herein, it will be appreciated by those skilled in the art to which the invention pertains, from a consideration of the foregoing description, that variations and modifications may be made without departing from the spirit and scope of the invention. For example, the specific physical characteristics of the coupling elements shown in the drawings are not absolutely essential, such as the alternating directions rather than a common direction of the longitudinal projections, as mentioned above, so long as they perform the function generally described herein. And as has already been noted, the stent design and functionality is not limited to a balloon-expandable stent, but may be employed with the so-called self-expanding stents that are formed for example from shape memory materials such as Nitinol. Accordingly, it is intended that the invention shall be limited only by the appended claims and the rules and principles of applicable law.

What is claimed is:

1. A stent of high longitudinal flexibility adapted to be implanted in a vessel, duct or tract of a human body to maintain an open lumen therein at a target site of final deployment, having a first small diameter unexpanded state for advancement to said target site and a second relatively larger diameter expanded state of deployment, said stent comprising a plurality of substantially identical rings commonly aligned in stacked configuration along a longitudinal axis of the stent, each of said rings including, in said unexpanded state, longitudinally projecting couplings adapted to mate pivotally with longitudinally projecting couplings of immediately adjacent rings, said rings being completely unattached to one another except through the pivotally mated couplings, whereby the rings in each pair of immediately adjacent rings may freely pivot longitudinally relative to one another.

2. The stent of claim 1, wherein each of said mated couplings is configured to undergo release in transition from said unexpanded state to said expanded state, whereby immediately adjacent pairs of said rings will undergo complete separation upon deployment of said stent, while maintaining their positional relation for supporting the lumen wall along said target site.

3. The stent of claim 2, wherein each of said rings includes a plurality of said couplings circumferentially positioned in spaced-apart relationship for mating in longitudinal pivotal relationship with corresponding couplings of at least one immediately adjacent ring.

4. The stent of claim 3, wherein said plurality of couplings on each ring reside on a respective plurality of longitudinal projections equally spaced-apart along and connected to a circular lateral element of the respective ring, said lateral element residing perpendicular to said longitudinal axis of the stent, said longitudinal projections each residing parallel to said longitudinal axis of the stent and including a pair of said couplings for mating with corresponding couplings of immediately adjacent rings at opposite sides thereof.

5. The stent of claim 2, wherein said couplings are configured to interlock loosely with mating couplings of immediately adjacent rings to enable said longitudinal pivoting relative to one another in said unexpanded state, and to withdraw from one another to enable said complete separation of the rings from each other during said transition to said expanded state.

6. The stent of claim 2, wherein said rings are dimensioned and composed of material to render the stent balloon-expandable.

7. The stent of claim 2, wherein said rings are dimensioned and composed of material to render the stent self-expandable.

8. A highly flexible stent with radial strength suitable for supporting a wall of a vessel, duct or tract of a body in which the stent is to be implanted against recoil of the wall in response to deployment of the stent, comprising a plurality of ring elements in stacked alignment along a longitudinal axis to form the basic configuration of the stent; and at least one coupling element on each of said ring elements configured and arranged to mate with and pivot longitudinally relative to at least a mating coupling element longitudinally aligned with said at least one coupling element on one of the neighboring ring elements, said stacked plurality of ring elements being held together only by mated pairs of the coupling elements while said stent is in an unexpanded state characterized by a relatively small ring element diameter.

9. The stent of claim 8, wherein said mated pairs of coupling elements are adapted to undergo a change in configuration sufficient to withdraw from their mated relationship to allow said ring elements to separate completely from each other when said stent is in transition from said unexpanded state to an expanded state having a relatively larger ring element diameter during deployment of the stent.

10. The stent of claim 9, wherein said at least one coupling element of each ring element is constructed to interlock loosely with at least one of the respective ones of said longitudinally aligned mating coupling elements of at least one of the neighboring ring elements to enable said longitudinal pivoting relative to one another in said unexpanded state, and to withdraw from the loose interlocking to enable said complete separation of the ring elements from each other during said transition to said expanded state.

11. The stent of claim 8, wherein said ring elements are dimensioned and composed of material to render the stent balloon-expandable.

12. The stent of claim 8, wherein said ring elements are dimensioned and composed of material to render the stent self-expandable.

13. A stent of high longitudinal flexibility, comprising multiple ring coupled together only by interlocking portions thereof to render the coupled ring elements articulating when the stent is in an unexpanded state, said ring elements being adapted to undergo deformation of said interlocking portions thereof so as to uncouple automatically while generally maintaining the positional relationship of the ring elements while the stent is being deployed to an expanded state.

14. A method for fabricating a highly flexible stent with radial strength suitable for supporting a wall of a vessel, duct or tract of a body in which the stent is to be implanted, against recoil of the wall in response to deployment of the stent, comprising the steps of forming a plurality of generally common ring elements in stacked alignment along a longitudinal axis; and fashioning coupling elements on each of said ring elements to mate with and pivot longitudinally relative to coupling elements fashioned on at least one of the neighboring ring elements as the only means holding the stack together.

15. The method of claim 14, including the step of constructing said coupling elements to deform and withdraw from their mated relationship while said ring elements are undergoing substantially uniform expansion in diameter during deployment of said stent, so that said ring elements will have separated completely from each other when said stent is in a fully expanded state.

16. The method of claim 15, including the steps of dimensioning said ring elements and composing them of material suitable to render the stent balloon-expandable.

17. The method of claim 15, including the steps of dimensioning said ring elements and composing them of material suitable to render the stent self-expandable.

18. The method of claim 14, including the step of forming the stack of said ring elements from a hollow tube while concurrently fashioning said coupling elements thereon in the mated relationship that holds the stack together.

19. The method of claim 14, including the steps of forming said ring elements individually, concurrently fashioning said coupling elements on each individual ring element, and thereafter loosely interlocking said coupling elements of neighboring ring elements in mated, longitudinal pivoting relationship while placing said ring elements in said stacked alignment along said longitudinal axis.

20. A vascular or endoluminal stent, comprising a longitudinally pivotable stack of ring elements at least all but the end elements of the stack being substantially identical to one another, said ring elements having interlocking portions constituting the only coupling holding said stack together, said interlocking portions being structured to undergo deformation to decouple during deployment of the stent, whereby to completely disjoin said ring elements from one another.

21. The stent of claim 20, wherein the ring elements are dimensioned and adapted to be retained in spaced-apart longitudinal alignment by expansion against the vascular or endoluminal wall along which the stent is deployed, despite said ring elements becoming completely disjoined from one another during deployment of the stent.

22. The stent of claim 21, wherein said ring elements, when coupled together in said longitudinally pivotable stack, render the stent sufficiently highly flexible longitudinally to traverse a tortuous vessel of a patient's body to a target site for deployment, and, when completely disjoined and retained against the vessel wall after deployment of the stent, provide high radial strength to resist recoil of the vessel wall and sufficiently complete decoupling to substantially avoid change of any natural curvature of the vessel at said site.

23. A stent comprising a plurality of interconnected generally circular bands of common diameter in longitudinal alignment along a common axis and constructed to undergo complete disconnect from one another in response to deployment of the stent and to substantially retain said longitudinal alignment in spaced-apart relation in captivity against a duct wall at the site of said deployment.

24. The stent of claim 23, wherein said bands are dimensioned and composed of material to render the stent balloon-deployable.

25. The stent of claim 23, wherein said bands are dimensioned and composed of material to render the stent self-deployable.

26. A stent comprising a plurality of juxtaposed rings having a common longitudinal axis, deformable couplings between said rings for loose interlocking thereof in free longitudinal articulation in a first radially compressed state, said couplings constructed and adapted to deform sufficiently for complete separation of the loosely interlocked rings into spaced-apart independent unitary elements substantially aligned along said common longitudinal axis under outwardly directed radial force exerted as the stent is deployed to a second radially expanded state at a preselected target site in a vessel, duct, tract or orifice to be held open by said elements.

27. The stent of claim 26, wherein said rings are dimensioned and of a composition to render the stent balloon-expandable.

28. The stent of claim 26, wherein said rings are dimensioned and of a composition to render the stent self-expandable.

29. A stent comprising an elongate flexible tube formed from radially expansible individual elements having pivotal interlocking portions to maintain longitudinal flexibility of the stent in a pre-deployed state, said interlocking portions constructed to undergo complete separation to free said individual elements into independent, generally parallel, self-supporting elements under radial expansion forces exerted upon deployment of the stent, for substantially equal distribution of biomechanical stress arising from support of a vessel wall over the entire length of the deployed stent.

30. The stent of claim 29, wherein each of said radially expansible individual elements is composed of a material to enable radial expansion thereof during deployment of the stent by inflation of a balloon catheter on which the stent is coaxially mounted, and to resist recoil of the vessel wall after deployment.

* * * * *